(12) United States Patent
Cong et al.

(10) Patent No.: US 10,835,126 B1
(45) Date of Patent: Nov. 17, 2020

(54) IMPLANTABLE MICRO-SPECTROPHOTOMETER

(71) Applicant: Verily Life Sciences LLC, Mountain View, CA (US)

(72) Inventors: Peng Cong, Cupertino, CA (US);
Travis J. Deyle, San Jose, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 878 days.

(21) Appl. No.: 14/934,620

(22) Filed: Nov. 6, 2015

(51) Int. Cl.
*A61B 5/00* (2006.01)

(52) U.S. Cl.
CPC .......... *A61B 5/0084* (2013.01); *A61B 5/0022* (2013.01); *A61B 5/0075* (2013.01); *A61B 5/441* (2013.01); *A61B 5/725* (2013.01); *A61B 2562/028* (2013.01); *A61B 2562/04* (2013.01)

(58) Field of Classification Search
CPC ..... A61B 5/0084; A61B 5/0075; A61B 5/441; A61B 5/0022; A61B 5/725; A61B 2562/04; A61B 2562/028
See application file for complete search history.

(56) References Cited

U.S. PATENT DOCUMENTS

| | | | |
|---|---|---|---|
| 6,431,175 B1 * | 8/2002 | Penner | A61N 5/1048 128/899 |
| 6,976,982 B2 * | 12/2005 | Santini, Jr. | A61F 9/0017 600/365 |
| 8,195,308 B2 | 6/2012 | Frank et al. | |

OTHER PUBLICATIONS

J.H. Correia et al., "Single-Chip CMOS Optical Microspectrometer," Sensors and Actuators 82 (2000) 191-197 (7 pages).

* cited by examiner

*Primary Examiner* — Mark Bockelman
(74) *Attorney, Agent, or Firm* — Kilpatrick Townsend & Stockton LLP

(57) ABSTRACT

The present disclosure relates to real-time in vivo spectrophotometric analysis of skin tissue. In some implementations, the spectrophotometry is implemented using a wireless microchip with at least one sensor implanted beneath the skin of an individual. The absorption of light at different wavelengths by the skin tissue is correlated to various skin states, revealing transient conditions or pathologies in real time. An external interrogation device is positioned on or adjacent to the surface of the skin and includes one or more energy sources for emitting light of different wavelengths. The external device may provide signals for wirelessly powering the implanted microchip, as well as have communication capabilities for receiving wireless transmissions from the implanted microchip. The sensors on the implantable microchip can be used to measure light intensity attenuated by the skin tissue between the light sources and the sensors. Each skin state has unique absorption characteristics at different frequencies, and property changes of the skin tissue (between the external light sources and the implantable microchip) affect power/intensity of light received by the light sensors at different frequencies.

10 Claims, 5 Drawing Sheets

IMPLANTABLE MICRO-SPECTROPHOTOMETER

BACKGROUND

The present disclosure generally relates to the measurement of light of one or more wavelengths passing through a medium as a means of characterizing the content or quality of the medium. More specifically, and without limitation, the present disclosure relates to micro-spectrophotometers and methods for using them implanted in the skin of a subject in order to collect information about the wearer's skin. In illustrative embodiments, one or more micro-spectrophotometers are implanted in an individual and, upon being supplied with an external source of illumination, the absorption at one or more wavelengths is determined. The absorption in illustrative embodiment can be used singly or in combination with other absorption measurements to determine a skin state of the individual implanted with the micro-spectrometer. Applying Beer's law, the amount of light absorbed by a medium at a specified wavelength is proportional to the concentration of the absorbing material or analyte present in the medium.

Spectrometers and spectrophotometers are optical devices which measure the amount of light absorbed or reflected by a material. Spectrometers measure which wavelengths are absorbed and which are reflected by a material, and spectrophotometers measure the relative intensity of light absorbed at a particular wavelength. A wide variety of spectrometers and spectrophotometers are useful in material analysis and characterization. Generally speaking, spectrometers and spectrophotometers each have the basic components of a light source and a detector for measuring the effect of the light's interaction with a material or materials.

By way of example, in spectrometry, a source may produce electromagnetic radiation, which could be, in order of increasing wavelength, ionizing radiation (such as extreme ultraviolet or X-rays), ultraviolet, visible or infrared light, microwaves or radio waves. The electromagnetic radiation is passed through a monochromator which narrows the wavelength of the electromagnetic radiation to a specified range to form an incident beam. The monochromator may be as simple as a filter, or may be a more complicated apparatus permitting tuning of the output to a specified wavelength or range of wavelengths. In some implementations, the source can be constructed so as to produce a single wavelength beam or an acceptably narrow range of wavelengths. The incident beam is passed through a sample and interacts optically through one or more of reflection, absorption and dispersion, resulting in an analytic beam. A detector can be used to receive the analytic beam and produces an output signal, which may be processed and/or displayed to a user.

In spectrophotometry, a source also produces electromagnetic radiation, such as ionizing radiation (such as extreme ultraviolet or X-rays), ultraviolet, visible or infrared light, microwaves or radio waves. The source can produce multiple or a range of wavelengths or can be constructed so as to produce a single wavelength beam or a narrow range of wavelengths. The electromagnetic radiation is passed through a sample, where it interacts with the sample through one or more of absorption, reflection or dispersion, resulting in analytic beam. The analytic beam can then be projected onto a diffraction grating which splits the analytic beam into one or more component beams. A detector can be used to receive the component beams and produce an output signal, which may be processed and/or displayed to a user.

Spectrometers and spectrophotometers are usable in laboratory settings where conditions can be controlled to avoid contamination of the various beams with external radiation. Conventional approaches also make use of transmissive photometry, where a radiation source and detector are placed on opposite sides of a sample. This is similar to the approach used in conventional pulse oximetry. The disadvantage of these configurations is that the signal path is longer than necessary to measure the epidermis. In pulse oximetry, the interrogating beam shone on the surface of the skin must traverse the entire finger, or in some embodiments the entire earlobe, in order to reach the detector. The longer the signal path, the more interactions the beam traversing tissue will have with various constituents of the tissue, attenuating the signal and introducing noise to the measurement. Measuring skin properties on the forearm, for instance, would require a beam to pass through the entire thickness of the forearm. The interrogating beam would need to be very powerful in this instance. Some have attempted to use reflectometry in optical measurements on the body, but these approaches also require a long signal path, which are complicated further by the fact that reflection is taking place at a very fine scale, so that large signal attenuations result in unusably low signal to noise ratios.

Spectrophotometry is applied in known pulse oximeters, which are used to calculate the oxygenation of blood. In transmissive pulse oximetry, two wavelengths of light are passed through a thin part of the body, such as the fingertip or earlobe. Changes in the measured absorbance at each of the wavelengths allows the identification of oxygenated blood passing during or shortly after systole of the heart. The technique allows the identification of the blood and the filtering out of noise from the signal due to absorption from surrounding tissue, bone, or other substances in the signal path. While useful in clinical settings for taking periodic measurements, transmission pulse oximetry requires a source of illumination and a sensor placed on opposite sides of a sample site. Therefore, the use of transmission spectrophotometry is not practical for long-term data acquisition on active patients. Because the measurement of arterial blood can be affected through a simple subtractive principle, allowing interfering absorbances to be disregarded and the signal of interest relatively easily identified, pulse oximetry has become a pervasive clinical tool. However its adaptation to other analytes that are not so readily isolated has been limited.

In reflectance pulse oximetry, an interrogating wavelength is introduced to a test site, and the light reflected is measured and processed to determine what amount of the incident light was absorbed by oxygenated blood. This approach is considered much more difficult, as certain spurious conditions can affect the optical measurement without being known, leading to unreliable results.

Devices known in the art used to analyze skin are based on techniques such as bio-impedance, ultrasound, or optical analysis using external device. Reliable results are difficult to achieve with these devices when movement occurs because of tissue interface difficulties, or because of the bulk of the devices. Some examples of commercially-available skin analysis products include DermaLab® from Cortex Technology and the skin sensor products of Moritex Corporation.

The optical properties of human skin are highly dependent on illumination source (including type and position), observer position and the skin surface structure. Most existing approaches use an illumination source and observer located outside the body. In such approaches, a number of confounding factors affect the received signal including, for example: material thickness (e.g., skin and other tissue); surface properties of the skin; and bulk effects of the muscle and/or fat rather than the skin. Also, these approaches often suffer from very low signal-to-noise levels since the light is massively attenuated or not much light is reflected when being emitted into large bodies of tissue.

SUMMARY

The present disclosure includes techniques and apparatus for collecting in-vivo information and analysis of skin tissue. In illustrative embodiments, a wearable device capable of producing real-time in-vivo optical measurements is implemented from a very small integrated circuit (microchip) implanted just beneath the skin. In some embodiments, a plurality of wireless microchip devices is used. In some embodiments, an external source supplies electromagnetic radiation to the implant.

Obtaining good measurements of skin absorption/transmission across a variety of optical wavelengths can provide valuable information about skin's water content, glucose concentrations, radiation exposure levels, blood perfusion, etc. Measuring these properties of skin condition can be useful for cosmetic applications (determining exposure to UV solar radiation, effectiveness of sunscreen or other creams, etc.), diagnosing skin disease, determining hydration levels, monitoring rashes, detecting heartbeat, etc. As another example, a spectrophotometer could measure the concentration of glucose in the skin's interstitial fluid.

In an illustrative embodiment, a microchip comprising an on-chip micro-spectrophotometer, a microprocessor including an analog-to-digital converter, and a wireless communications circuit, is implanted in the skin of a wearer at a specified depth. The spectrophotometer can be broad-band, or can be patterned with, or otherwise provided with, a filter for sensitivity to a specific wavelength or range of wavelengths. When interrogated with an external source of known intensity and/or wavelength, the implanted microchip wirelessly transmits a digital signal containing optical measurements made by the micro-spectrophotometer, from which optical absorption/transmission can be calculated.

In other embodiments, a plurality of implanted microchips are employed beneath the skin of an individual, which can provide optical properties at different locations, as well as optical properties at other wavelengths, if so configured. In other embodiments, a microchip carries a plurality of photodetectors.

In exemplary embodiments, information on skin water content, skin condition, and analyte concentration such as glucose or glycated hemoglobin can be collected. Blood perfusion could also be assessed over time or over an area of the skin.

In another exemplary embodiment, the sensor could provide skin hydration information over time. Such information can help determine the effectiveness of certain variables in a patient's lifestyle, such as the use of moisturizers, medications, relative environmental humidity, etc. as well as aggregate or transient exposures over a long or short time frame.

In other exemplary embodiments measurements of skin absorption/transmission across a variety of optical wavelengths provide valuable information about radiation exposure levels, blood perfusion, etc. Measuring these properties of skin condition can be further useful for a variety of cosmetic or health applications, such as determining exposure to UV solar radiation, the extent of a suntan or the occurrence of sunburn, and the effectiveness of sunscreen.

In still further illustrative embodiments, the implanted microchips can assist in the diagnosing or spread of skin disease and rashes.

As another example, an implantable micro-spectrophotometer could measure the concentration of glucose in the skin's interstitial fluid.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXEMPLARY EMBODIMENTS

Figure 1:
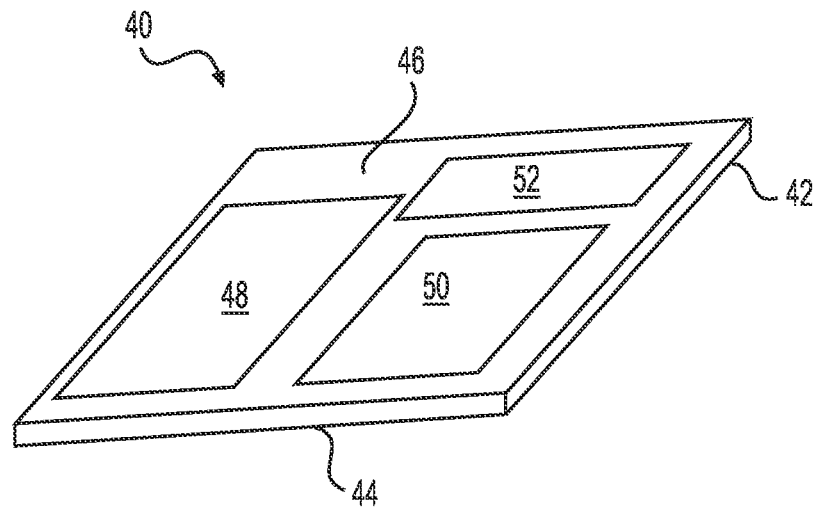
FIG. 1 illustrates an exemplary implantable microchip according to the present disclosure.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, it is to be appreciated that the drawings may not be to scale. Moreover, the words "exemplary" or "illustrative" are used herein to mean serving as an example, instance, or illustration. Any aspect or design described herein as "exemplary" or "illustrative" is not necessarily to be construed as preferred or advantageous over other aspects or designs.

While moisture (water) detection in the skin is discussed herein, other analytes, constituents, chromophores, metabolites or substances of interest can be detected. With the proper selection of wavelength, the present disclosure can be used to detect or characterize other substances of interest such as melanin, hemoglobin, amino acids, urocanic acid, bioluminescent markers, etc. The devices, systems and methods according to the present disclosure can also be used to detect and/or monitor light penetration into the skin of various wavelengths, such as UVA and UVB.

Embodiments of the present disclosure solve the above-referenced problems with conventional spectrometers and spectrophotometers through the use of an implantable microchip having an optical sensor, which can be spectrometric or spectrophotometric in operation. An illustrative embodiment of an implantable microchip is described below with reference to FIG. 1. As further described below, an implantable microchip 40 can be dimensioned for placement in vivo in the epidermis of a wearer at a known or knowable depth, to provide optical measurements of the skin using an external source of electromagnetic radiation, such as an LED light source. By measuring the illuminance of the light at the sensor of the microchip at one or more wavelengths, the properties of the skin can be instantly and reliably ascertained. The microchip may include a variety of circuits for powering, wireless communication, etc. as well as a photodetector that is sensitive to desired wavelengths. The microchip is dimensioned so as to introduce minimal discomfort during and after implantation.

FIG. 1 shows an illustrative implantable integrated microchip 40, dimensioned for placement in the epidermis of a wearer. The microchip can be dimensioned to introduce minimal discomfort during and after implantation. By way of example, in some embodiments, microchip 40 is dimensioned to have a width 42 and a length 44 each between about 100μ to 500μ. The substrate 46 can be made of monocrystalline silicon, gallium arsenide or other semiconductor that is biocompatible such as single-crystal silicon carbide. The microchip can be formed according to known processes of deposition, removal, patterning, and modification of electrical properties as required. In addition, the microchip is packaged as required to allow biocompatibility and implantation.

The circuits on the microchip 40 can include a photodetector array 48, a power management circuit 50 and a wireless communications circuit 52. Other circuits may also be included on the microchip 40, such as a microprocessor with analog-to-digital (A/D) conversion and other capabilities. In other embodiments, the microchip 40 includes individual or dedicated circuits for each capability, such as an A/D circuit, low-pass analog filtering, amplification, etc. Each of the circuits on the microchip, including circuits 48, 50, 52, may be connected to a common system bus. The photodetector array 48 can have one or more photodiodes or other light detectors, such as ferroelectric photodetectors, that each function as a sensor. The power management circuit 50 can be self-powered using a small battery or rechargeable capacitor, or could facilitate power transfer transdermally from an external device or other powering unit. In some embodiments, the power management circuit 50 can contain photovoltaic devices for generating power. The wireless communications circuit 52 controls transmission of data according to established protocols to an external device. In some embodiments, the wireless communications circuit 52 is capable of transmitting data using radio frequency (RF) signals. In other embodiments, data signals are wirelessly transmitted by circuit 52 using other wavelengths or protocols, such as Bluetooth. The chip 40 can include conversion of photodetector outputs to digital signals, as well as data buffering or recording for storing the digital signal prior to transmission.

In illustrative embodiments, photodetector array 48 can include a plurality of photodetectors, which can be configured to measure the same or different wavelengths. As will be appreciated from this disclosure, various approaches may be utilized for tuning a photodiode to respond to a specific wavelength or range of wavelengths, referred to herein generically as providing a "filter" or "filtering." For example an optical film, coating or layer may be provided over the photodiode to only admit the desired wavelength(s). These approaches to photoselectivity can be implemented after manufacturing of the semiconductor chip. Calibration during manufacturing can also be used to tune the response of photodetectors to a desired wavelength or wavelength range. The choice of which diodes to use will also effect photo-sensitivity (e.g., P-Well, N-Well, Deep N-Well, etc.). In addition, the doping properties of the semiconductor can play a role in spectral sensitivity. Optical response can also be modified by metallization atop or near the diode. It is also possible to employ coatings to the photodiode(s) that permanently change their optical properties (e.g., transmissivity) in response to exposure to a specific electromagnetic radiation. In an exemplary embodiment, the back side of the photodiode is metallized.

In an exemplary embodiment, a thin-film UV-curing photopolymer that changes color or opacity could coat one or more photodiodes, while others are not so coated. This allows the spectrophotometer to advantageously measure aggregate UV exposure, for example, without having to store or buffer individual readings, because the difference in the measurements between the coated and uncoated photodiodes would correlate to aggregate exposure. In other exemplary embodiments, a coating could be responsive, over short or long time periods, to body metabolites, proteins, or constituents such as blood alcohol or specific drugs. Advantageously, illustrative embodiments using changeable coatings permit an external source of electromagnetic energy to query for aggregate exposure as well as transient events or events that take place while the chip is not being actively monitored.

Figure 2:
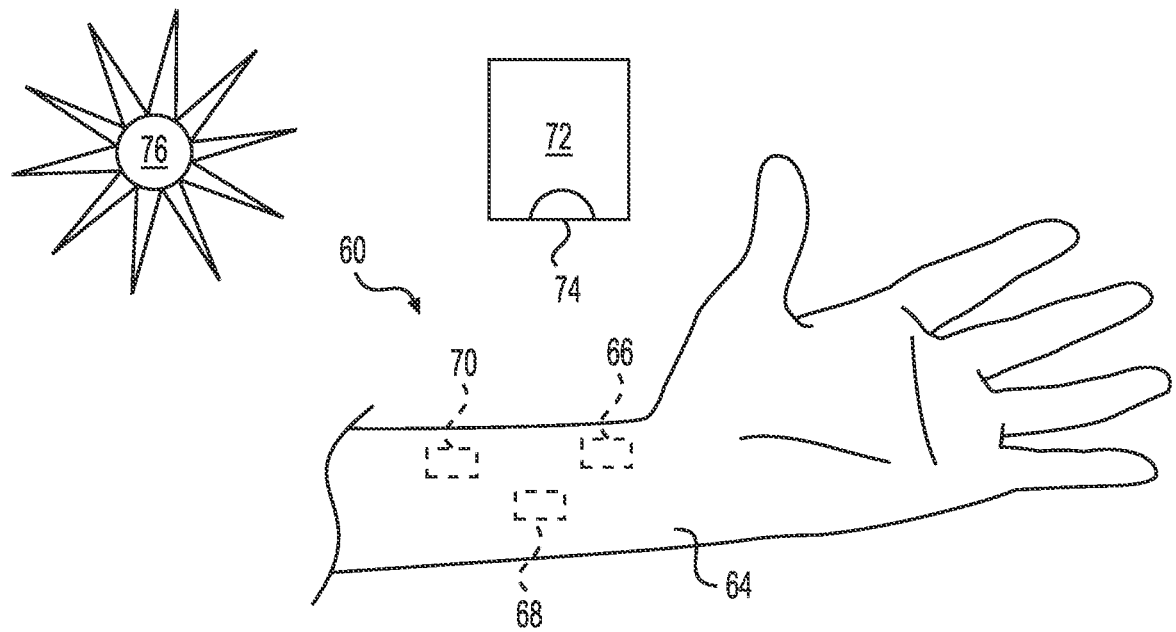
FIG. 2 depicts an exemplary system for using the exemplary implantable microchip depicted in FIG. 1.

FIG. 2 shows an illustrative system 60 for using the exemplary microchip 40 of FIG. 1. According to illustrative system 60, three exemplary wireless chips 66, 68, 70 are implanted at different locations on the forearm 64 of an individual for measuring properties of the skin. These chips can be the same, or different, and can be provided with photodetectors tuned to either a single or multiple wavelengths. As will be appreciated from this disclosure, any number of chips can be employed, and the choice of three is illustrative. In some embodiments, each microchip 66, 68, 70 can provide a different channel of information either by location (lateral or depth) or by its configuration (e.g., wavelength sensitivity).

External device 72 is provided with an electromagnetic energy source 74 for supplying an interrogating beam to wireless microchips 66, 68, and 70. The external device 72 can include one or more light sources of various wavelengths, as well as circuitry for powering and communication. The source 74 can be single or multiple wavelengths. While illustrated as an integral unity, external unit 72 can have its functional elements residing in separate or separable housings, e.g., the energy source 74 can be separate from the communications and powering components. In one illustrative system, the energy source 74 can supply a range of wavelengths of light of known intensity, and the microchips 66, 68, 70 can be tuned to measure only a single wavelength. In another illustrative system, the microchips 66, 68, 70 can be tuned to measure a range of wavelengths, and the energy source 74 supplies one or more wavelengths of known intensity, either together or in series. A sweep of wavelengths can also be performed. The combination of microchips and their wavelength sensitivity with the energy source provides for various test protocols and various data to be gathered. Alternatively, or in addition to the energy source 74, an ambient light source 76 such as the sun can be employed as the interrogating beam. Using the sun in this manner can advantageously help to measure UV exposure, for example, or monitor the presence of chromophores such as melanin, or both over time.

The external device 72, in an illustrative embodiment, emits light into the skin of the individual with the one or more implantable microchips. The light passes through the skin, where it undergoes attenuation and scattering depending on the physical properties of the skin tissue between the external device and the microchip. The microchip then measures the amount of light incident on its photodetector and wirelessly communicates this information back to the external device. This process may be repeated for a number of different wavelengths. The external device (or the microchip) can use the spectral information to extract information about skin tissue. Properties of the skin and associated tissue (e.g. chemical makeup of interstitial fluids, blood flow, and other structures in the skin such as fat, hair follicles, etc.) will affect the illuminance measured by the implanted microchip. Employing multiple wavelengths of emitted light can provide the skin's optical response as a function of radiation wavelength. Certain properties of the skin ("skin states") result in unique spectral absorption characteristics. For example, water has an absorption peak around 900 nm; the amount of light emitted by the external device and received by the microchip at this wavelength will vary depending on the moisture level of the skin. Hydration levels (and changes in hydration) can thus be determined using the 900 nm light source.

Electromagnetic radiation source 74 can be monochromatic (as with a laser diode) to obtain very precise absorption information for a single wavelength. Single color LEDs, where the emitted light occupies a band of wavelengths (e.g., IR, Red, Green, Blue, UV) can also be employed. In this case, photodiode measurements are effectively aggregated over a broader set of wavelengths. Broad spectrum LEDs (e.g., white LEDs), which occupy a large band of wavelengths can also be employed, and again, photodiode measurements from these sources are effectively aggregated over a broad set of wavelengths.

Figure 3:
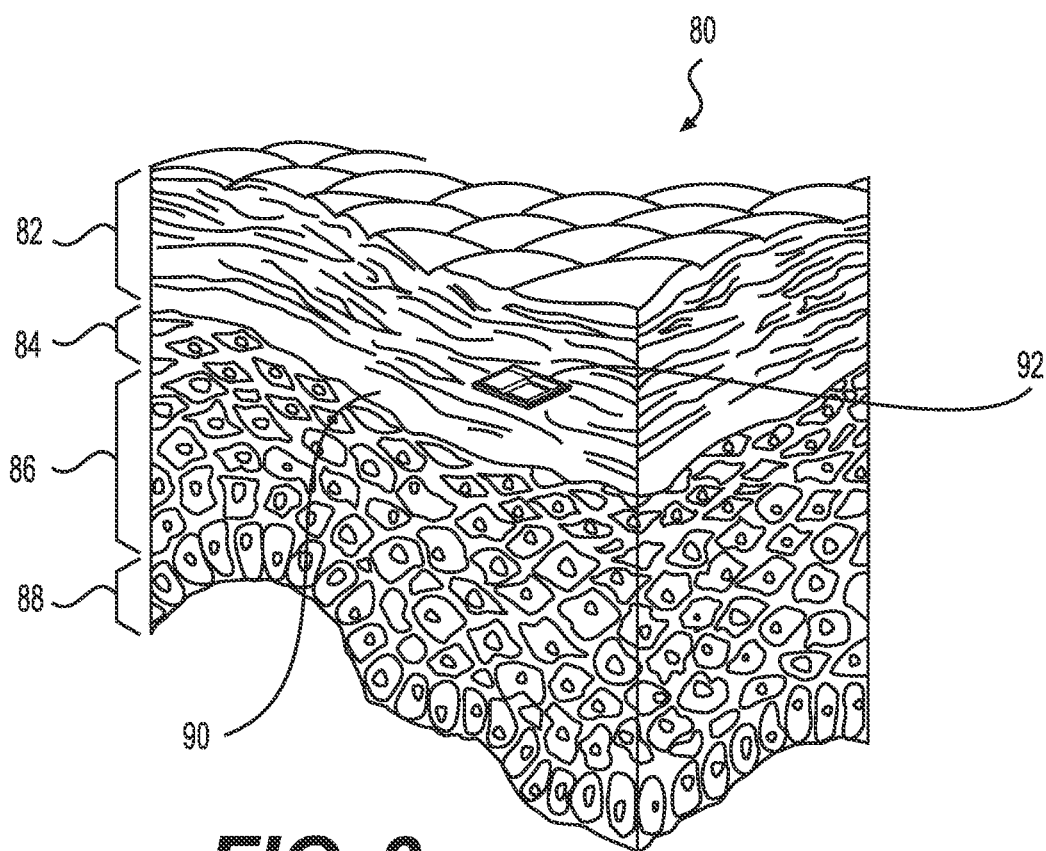
FIG. 3 depicts a cross-section of the human epidermis with an exemplary wireless microchip implanted therein.

Turning now to FIG. 3, a cross-section of human epidermis 80 is shown including an implanted microchip 92, according to the instant disclosure. The surface layer of skin is known as the stratum corneum 82, which formed from 15 to 20 layers of dead compressed corneocytes. The next layer is the stratum granulosum 84, which is a thin layer of granular cells containing keratohyalin granules. Next comes the stratum spinosum 86, formed of polyhedral keratinocytes. At the base of the epidermis is the stratum basale 88, which overlies the dermis and is formed of basal keratinocyte stem cells. An additional layer present in thick skin layers in the body is the clear stratum lucidum 90. One or more of the microchips 92 can be implanted at any stratum, according to the analytic protocol being followed.

Figure 4:
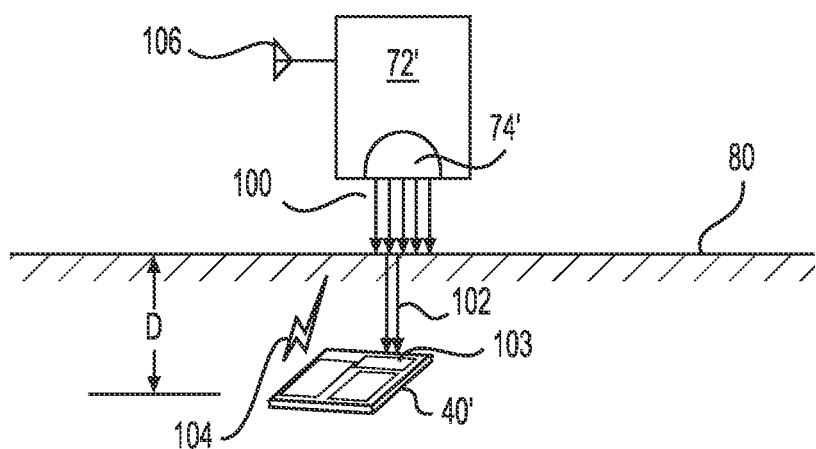
FIG. 4 depicts an exemplary system for using an exemplary implantable microchip.

FIG. 4 shows a schematic representation of an illustrative system employing exemplary wireless microchips according to the present disclosure. Microchip 40' is implanted beneath the surface of epidermis 80 at a depth D. An external device 72' having an electromagnetic source 74' applies a beam of electromagnetic energy 100 to a region proximate to microchip 40'. The electromagnetic energy can be applied continuously or in a modulated or pulsed manner. As electromagnetic energy 100 passes through the epidermis 80 through a depth D, it interacts with the tissue and substances contained therein, before reaching the microchip 40' at sensor contact point 103. The photodetector reacts to the energy at point 103 and generates a sensor output electrical signal. After any on-chip processing of the sensor output signal, an RF signal 104 containing data derived from the sensor output is generated and transmitted. In an illustrative embodiment, an antenna 106 on the external device 72' receives the RF signal 104. In other embodiments, other forms of wireless signals are used to transmit the sensor data, such as Bluetooth signals.

Figure 5:
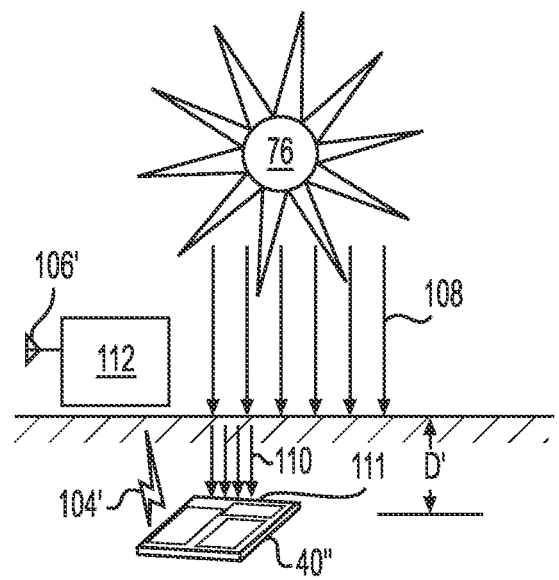
FIG. 5 depicts a further exemplary system for using an exemplary implantable microchip.

FIG. 5 shows a schematic representation of a further illustrative system employing exemplary microchips according to the present disclosure. Microchip 40" is implanted beneath the surface of epidermis 80 at a depth D'. An ambient source of electromagnetic radiation, such as the sun 76, supplies a beam of electromagnetic energy 108 to a region proximate to microchip 40". The electromagnetic energy can be applied directly to the epidermis 80 unfiltered, or through filters or filtering agents such as sunblock. As electromagnetic energy 110 passes through the epidermis 80 through a depth D, it interacts with the tissue and substances contained therein, before reaching the microchip 40" at sensor contact point 111. The photodetector reacts to the energy at point 111 and generates a sensor output electrical signal. After any on-chip processing of the sensor output signal, an RF signal 104' containing data derived from the sensor output is generated and transmitted. In an illustrative embodiment, an antenna 106' on external device 112 receives the RF signal 104'. In other embodiments, other forms of wireless signals are used to transmit the sensor data, such as Bluetooth signals.

Figure 6:
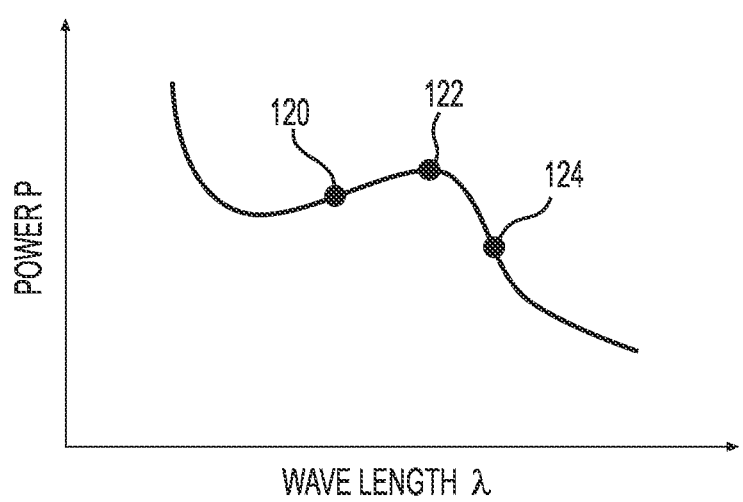
FIG. 6 is a graph showing an exemplary wavelength-to-power response curve measured by an exemplary system according to the present disclosure.

FIG. 6 is a graph showing an exemplary wavelength-to-power response curve measured by an exemplary system according to the present disclosure. The y-axis represents power/intensity P of light at the sensor, while the x-axis represents the wavelength of the electromagnetic energy. In the illustrative response curve, points 120, 122 and 124 represent the different power/intensity measures at the sensor corresponding to three different wavelengths, respectively, as the wavelength increases. The points 120, 122 and 124 can be gathered simultaneously or at separate times. The measure of power/intensity, or irradiance, is itself illustrative. In a sensor using a photodiode, the response of the diode to incident radiation, expressed in A/W is usually not linear, and will be corrected according to a calibration formula or algorithm for the particular sensor.

Figure 7:
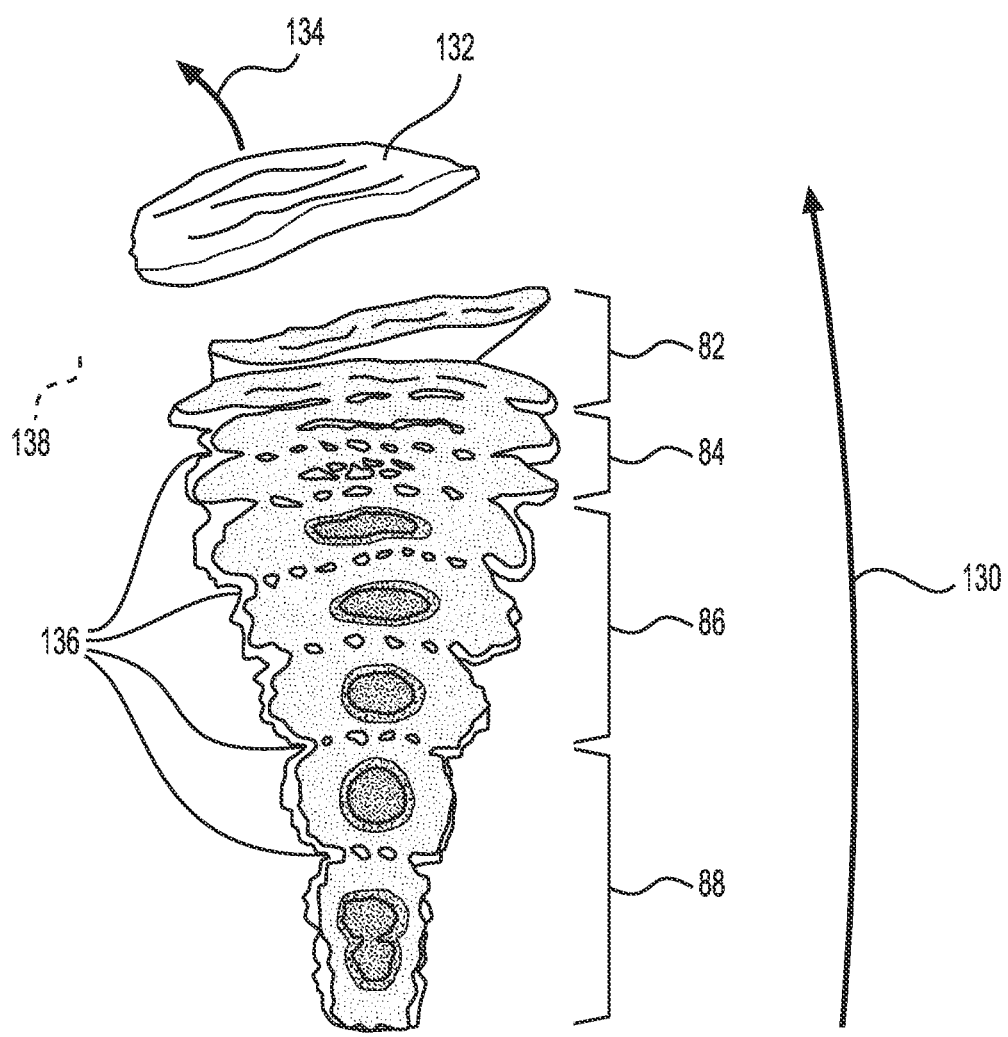
FIG. 7 depicts an exemplary use of aspects of the present invention in a representative skin cell desquamation process.

In a further exemplary application of wireless microchips 40, 40', 40" of the present disclosure, the chips can be dimensioned and placed so as to traverse one or more of the different layers 82, 84, 86, 88 and/or 90 of the epidermis during a skin cycle 130 as shown in FIG. 7. A skin cycle is the time it takes for nascent skin cells to be born at the stratum basale 88, and mature as they rise to the stratum corneum 82, and ultimately are shed off 134 as dead cells 132 in a process called desquamation. This process takes anywhere from three to six weeks. Advantageously, in an exemplary embodiment, microchips according to the present disclosure can be implanted at layers 136 within or between the strata of the skin and be advanced toward the surface 138 during the skin cycle. The chips are sloughed off during desquamation after providing skin state data over time at each stage of the skin cycle.

Figure 8:
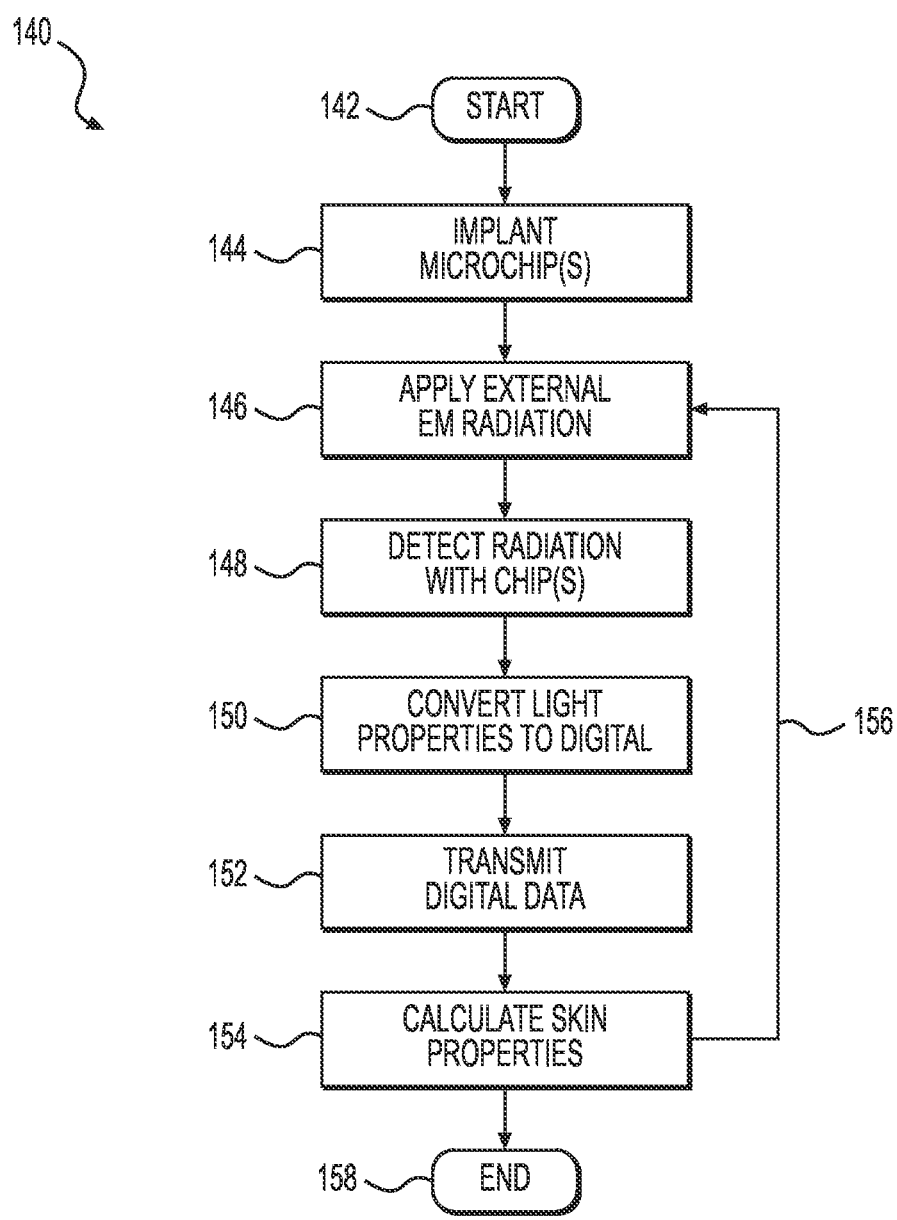
FIG. 8 is a flowchart of an exemplary process according to the present disclosure.

FIG. 8 depicts an illustrative process 140 according to the present disclosure. The exemplary process 140 may be implemented with the systems of above embodiments. As shown in FIG. 8, the process begins at 142, where one or more microchips 40, 40', 40" are implanted beneath the skin of an individual. If multiple microchips are used, they may be implanted at different locations under the skin (see, e.g., FIG. 2). An external source of electromagnetic radiation is applied at 146, and detected by each implanted microchip approximate to the source at 148. The radiation incident upon one or more sensors of each microchip is converted to a digital signal at 150, and wirelessly transmitted at 152. The transmitted signals are then received and processed to determine one or more skin properties at 154. This process is repeated, as needed, at 156 as dictated by the experimental protocol. The process ends at 158.

The microchips 40, 40' and 40" can also be provided with commands, software updates, etc. from an external source via RF, Bluetooth, or another band or protocol, whereby the wireless communications circuit 52 would be bi-directional and be outfitted with an antenna or other signal receiving device. The RF or other signal provided to the chip can also be used to provide other operational inputs, such as a system clock signal, wake-up command, transmit requests, date transfer sequencing between plural chips, calibration information, etc.

The methods and systems described herein may transform physical and/or or intangible items from one state to another.

The elements described and depicted herein, including in the flow chart and block diagrams throughout the figures, imply logical boundaries between the elements. However, the depicted elements and the functions thereof may be implemented simultaneously, in parallel or in series where appropriate. Thus, while the foregoing drawings and descriptions set forth functional aspects of the disclosed systems, no particular arrangement of these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application, e.g., through automation. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

Any computer-executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While embodiments of the present disclosure have been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A system for spectrophotometric analysis of skin tissue of an individual, the system comprising:
    a microchip configured to be implanted under the surface of the skin comprising:
        a photodetector configured to receive electromagnetic radiation in the optical spectrum including infrared and ultraviolet light, and output a signal indicating an amount of received electromagnetic radiation in the optical spectrum; and
        a wireless transmitter to transmit the amount of received electromagnetic radiation to a remote device;
        wherein the microchip is configured to, in response to receiving the signal:
            determine the amount of received electromagnetic radiation, and
            cause the wireless transmitter to transmit an indication of the amount of received electromagnetic radiation; and
    wherein the microchip is sized to be implanted within a patient's skin and to be sloughed off during desquamation.

2. The system of claim 1, further comprising an optical filter configured and arranged to allow substantially a single wavelength of the optical spectrum to reach the photodetector.

3. The system of claim 1, further comprising an optical filter configured to allow substantially a single color of the optical spectrum over a range of wavelengths to reach the photodetector.

4. The system of claim 1, wherein said microchip comprises a plurality of photodetectors, each photodetector of the plurality of photodetectors configured to receive electromagnetic radiation in the optical spectrum including infrared and ultraviolet light.

5. The system of claim 1, further comprising a plurality of microchips, wherein each microchip of the plurality of microchips is implanted at a different location under the surface of the skin of the individual, and wherein each microchip comprises a photodetector configured to receive configured to receive electromagnetic radiation in the optical spectrum including infrared and ultraviolet light and output a signal indicating an amount of received electromagnetic radiation; and a wireless transmitter to transmit the amount of received electromagnetic radiation to a remote device.

6. The system of claim 5, wherein at least two microchips of the plurality of microchips are tuned for different wavelengths or ranges of wavelengths.

7. The system of claim 6, wherein a first of the at least two microchips is tuned for UVA light and a second of the at least two microchips is tuned for UVB light.

8. The system of claim 1 further comprising:
a microprocessor configured to:
calculate, based on the signal from the photodetector, the absorption of ambient radiation of at least one wavelength; and
output the calculated absorption.

9. The system of claim 1, wherein the microchip has a width between 100 microns and 500 microns and a length between 100 microns and 500 microns.

10. The system of claim 1, further comprising a reader device comprising a light emitter and a wireless receiver, the reader device configured to:
emit one or more wavelengths of electromagnetic radiation in the optical spectrum including infrared and ultraviolet light; and
receive, from the microchip, the indication of the amount of received electromagnetic radiation,
wherein the indication of the amount of received electromagnetic radiation indicates an amount of at least one wavelength of the one or more wavelengths of light received by the microchip.

* * * * *